(12) United States Patent
Chen

(10) Patent No.: US 10,729,817 B2
(45) Date of Patent: Aug. 4, 2020

(54) MEDICAL DEVICE AND PLASTICIZED NYLON

(71) Applicant: Medtronic Vascular, Inc., Santa Rosa, CA (US)

(72) Inventor: Mingfei Chen, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 16/037,919

(22) Filed: Jul. 17, 2018

(65) Prior Publication Data

US 2018/0318470 A1 Nov. 8, 2018

Related U.S. Application Data

(63) Continuation of application No. 13/829,913, filed on Mar. 14, 2013, now Pat. No. 10,052,413.

(51) Int. Cl.
| | |
|---|---|
| *A61L 29/06* | (2006.01) |
| *A61L 29/14* | (2006.01) |
| *C08K 5/20* | (2006.01) |
| *C08L 29/06* | (2006.01) |
| *A61F 2/95* | (2013.01) |
| *C08K 5/00* | (2006.01) |

(52) U.S. Cl.
CPC ............ *A61L 29/06* (2013.01); *A61F 2/95* (2013.01); *A61L 29/141* (2013.01); *C08K 5/20* (2013.01); *C08K 5/0016* (2013.01)

(58) Field of Classification Search
None
See application file for complete search history.

(56) References Cited

U.S. PATENT DOCUMENTS

| | | |
|---|---|---|
| 2,452,313 A | 10/1948 | Morgan |
| 3,142,653 A | 7/1964 | Blackman et al. |
| 3,284,187 A | 11/1966 | Lidner |
| 3,475,365 A | 10/1969 | Silverman |
| 3,700,624 A | 10/1972 | Adachi et al. |
| 3,787,457 A | 1/1974 | Mod et al. |
| 4,565,849 A | 1/1986 | Horikawa et al. |
| 5,496,918 A | 3/1996 | Khanna et al. |
| 5,541,267 A | 7/1996 | Akkapeddi et al. |
| 5,948,345 A | 9/1999 | Patel et al. |
| 6,348,563 B1 | 2/2002 | Fukuda et al. |
| 6,860,930 B2 | 3/2005 | Wu et al. |
| 7,786,222 B2 | 8/2010 | Schmid et al. |
| 7,858,074 B2 | 12/2010 | Caron et al. |
| 7,893,140 B2 | 2/2011 | Hase |
| 2007/0020446 A1 | 1/2007 | Niino et al. |

(Continued)

FOREIGN PATENT DOCUMENTS

| | | |
|---|---|---|
| DE | 10 2005 057 196 A * | 6/2007 |
| EP | 0974575 | 1/2000 |

(Continued)

OTHER PUBLICATIONS

English abstract of DE 102005057196 A, Jun. 6, 2007, Germany, 7 pages.*

(Continued)

*Primary Examiner* — Tae H Yoon

(57) ABSTRACT

A medical device, such as a dilatation balloon, including plasticized nylon, and plasticized nylon.

20 Claims, 6 Drawing Sheets

(56) References Cited

U.S. PATENT DOCUMENTS

| | | | |
|---|---|---|---|
| 2009/0131674 A1 | 5/2009 | Schmid et al. |
| 2009/0238854 A1 | 9/2009 | Pacetti et al. |
| 2010/0262218 A1 | 10/2010 | Deshmukh |
| 2011/0257577 A1 | 10/2011 | Lane et al. |
| 2013/0023613 A1 | 1/2013 | Klatt et al. |
| 2014/0277337 A1 | 9/2014 | Chen |

FOREIGN PATENT DOCUMENTS

| | | | |
|---|---|---|---|
| GB | 845494 | * | 8/1960 |
| JP | 56067346 | | 6/1981 |
| JP | 01242667 | | 9/1989 |
| JP | 401242667 | | 9/1989 |
| JP | 2009/298857 | | 12/2009 |
| WO | WO 98/36783 | | 8/1998 |

OTHER PUBLICATIONS

American Society of Testing Materials, ASTM D638, "Standard Test Method for Tensile Properties of Plastics" May 15, 2010; 16 pgs.

J.B. Williams et al. "Structure/Performance Characteristics of Bisamide Lubricants in ABS" Journal of Vinyl and Additive Technology. Sep. 1, 1997, vol. 3, Issue 3, pp. 216-219.

PCT/US2014/026534, Communication Relating to the Results of Partial International Search, dated Jun. 13, 2014.

Van Krevelen, *Properties of Polymers, 3rd Edition*, Amsterdam, the Netherlands, 1990; cover page, title page and table of contents only, 8 pgs.

\* cited by examiner

MEDICAL DEVICE AND PLASTICIZED NYLON

This application is a continuation of U.S. patent application Ser. No. 13/829,913, filed Mar. 14, 2013, now U.S. Pat. No. 10,052,413, the disclosure of which is incorporated herein by reference thereto.

BACKGROUND OF THE DISCLOSURE

Many medical devices, particularly balloons and catheters used in angioplasty procedures are made from polyamides such as various nylons. Such polymers are often relatively stiff for some delivery systems and processes.

The unique conditions under which balloon dilatation is performed typically require extremely thin-walled, high-strength balloons that, when deflated, are flexible and trackable enough to be maneuvered through small, tortuous vessels. Balloons made from high-strength polymers, while exhibiting high burst strengths, exhibit less flexibility and trackability than desired. The addition of a plasticizer to the materials increases the softness and flexibility of the balloon; however, the use of plasticizer can limit the balloons applicability as a bio-compatible material. Balloons that exhibit high burst strengths that can be used in stent delivery, but also exhibit high flexibility and trackability, are desired. New balloon materials are therefore needed to tailor the properties of the balloon and produce high-strength and highly flexible balloons for medical applications.

SUMMARY OF THE DISCLOSURE

In one embodiment, the present disclosure provides a medical device that includes a plasticized nylon, wherein the plasticized nylon includes a nylon and an amide-containing plasticizer selected from a compound having the following structural formulas:

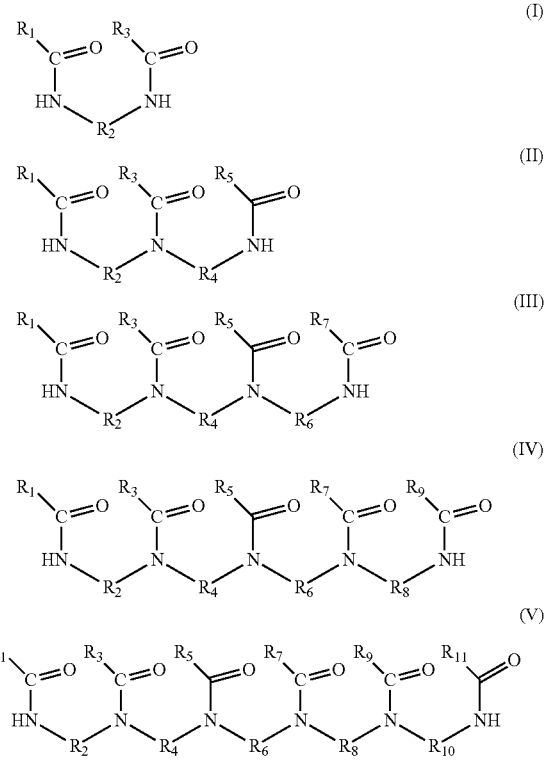

and combinations thereof; wherein:

each $R_1$, $R_3$, $R_5$, $R_7$, $R_9$, and $R_{11}$ is independently selected from a C2-C18 linear, branched, or cyclic monovalent aliphatic group (preferably, an alkyl group), optionally including unsaturation and/or functional groups of amide, ester, hydroxyl, phosphate groups, or combinations thereof, a C5-C12 monovalent aromatic group, and combinations thereof; and each $R_2$, $R_4$, $R_6$, $R_8$, and $R_{10}$ is independently selected from a C2-C18 linear, branched, or cyclic divalent aliphatic group (preferably, an alkylene group), optionally including unsaturation and/or functional groups of amide, ester, hydroxyl, phosphate groups, or combinations thereof, a C5-C12 divalent aromatic group, and combinations thereof.

In another embodiment, the present disclosure provides a medical device including a plasticized nylon, wherein the plasticized nylon includes Nylon-12 and an amide-containing plasticizer having the following structural formula:

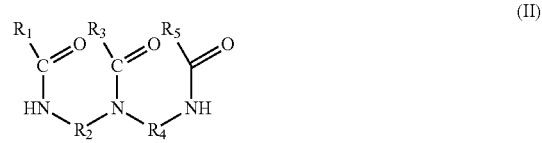

wherein:

each $R_1$, $R_3$, and $R_5$ is independently selected from a C2-C18 linear, branched, or cyclic alkyl group, a C5-C12 monovalent aromatic group, and combinations thereof; and each $R_2$ and $R_4$ is independently selected from a C1-C5 linear alkylene group, a C5-C12 divalent aromatic group, and combinations thereof.

In another embodiment, the present disclosure provides a balloon dilatation catheter including:

a tubular elongated catheter shaft having proximal and distal portions; and a dilatation balloon disposed on said shaft, wherein the shaft and/or balloon includes a plasticized nylon, wherein the plasticized nylon includes Nylon-12 and an amide-containing plasticizer having the following structural formula:

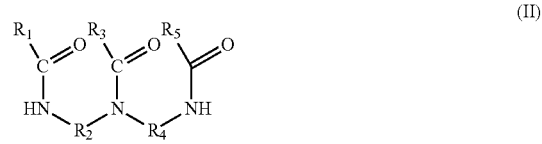

wherein:

each $R_1$, $R_3$, and $R_5$ is independently selected from a C2-C18 linear, branched, or cyclic alkyl group, a C5-C12 monovalent aromatic group, and combinations thereof; and each $R_2$ and $R_4$ is independently selected from a C1-C5 linear alkylene group, a C5-C12 divalent aromatic group, and combinations thereof.

In another embodiment, the present disclosure provides a plasticized nylon, wherein the plasticized nylon includes a nylon and an amide-containing plasticizer selected from a compound having one of the structures (I) through (V) and combinations thereof, as described above.

As used herein, "aliphatic group" means a saturated or unsaturated linear (i.e., straight-chain), branched, cyclic (including bicyclic) organic group. This term is used to encompass alkyl, alkenyl, and alkynyl groups, for example. Herein, the term "aliphatic group" also includes "alicyclic group," which encompasses a cyclic hydrocarbon group having properties resembling those of an aliphatic group.

The term "aromatic group" or "aryl group" means a mono- or polynuclear aromatic hydrocarbon group (e.g., phenyl).

As used herein, "alkyl group" refers to a monovalent group that is a radical of an alkane and includes straight-chain, branched, cyclic (including bicyclic) organic groups, and combinations thereof, including both unsubstituted and substituted alkyl groups. Unless otherwise indicated, the alkyl groups typically contain from 2 to 18 carbon atoms. In some embodiments, the alkyl groups contain 2 to 10 carbon atoms, 2 to 6 carbon atoms, 2 to 4 carbon atoms, or 2 to 3 carbon atoms. In some embodiments, the alkyl groups contain 6 to 12 carbon atoms, or 7 to 8 carbon atoms. Examples of "alkyl" groups include, but are not limited to, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, norbornyl, and the like.

The term "alkylene group" refers to a divalent group that is a radical of an alkane and includes groups that are linear, branched, cyclic (including bicyclic) organic groups, and combinations thereof, including both unsubstituted and substituted alkyl groups. Unless otherwise indicated, the alkylene group typically has 2 to 18 carbon atoms. In some embodiments, the alkylene group has 2 to 10 carbon atoms, 2 to 6 carbon atoms, or 2 to 4 carbon atoms. Examples of "alkylene" groups include ethylene, 1,3-propylene, 1,2-propylene, 1,4-butylene, 1,4-cyclohexylene, and 1,4-cyclohexyldimethylene.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As used herein, "a," "an," "the," "at least one," and "one or more" are used interchangeably. Thus, for example, "a" plasticized nylon that includes "a" nylon and "a" plasticizer can be interpreted to mean that "one or more" nylons and "one or more" plasticizers. As used herein, the term "or" is generally employed in its sense including "and/or" unless the content clearly dictates otherwise. The term "and/or" means one or all of the listed elements or a combination of any two or more of the listed elements.

As used herein, all numbers are assumed to be modified by the term "about" and preferably by the term "exactly." Notwithstanding that the numerical ranges and parameters setting forth the broad scope of the disclosure are approximations, the numerical values set forth in the specific examples are reported as precisely as possible. All numerical values, however, inherently contain certain errors necessarily resulting from the standard deviation found in their respective testing measurements. Also herein, the recitations of numerical ranges by endpoints include all numbers subsumed within that range (e.g., 1 to 5 includes 1, 1.5, 2, 2.75, 3, 3.80, 4, 5, etc.).

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The disclosure may be further illustrated by reference to the accompanying Drawings wherein.

DETAILED DESCRIPTION OF ILLUSTRATIVE EMBODIMENTS OF THE DISCLOSURE

Figure 1:
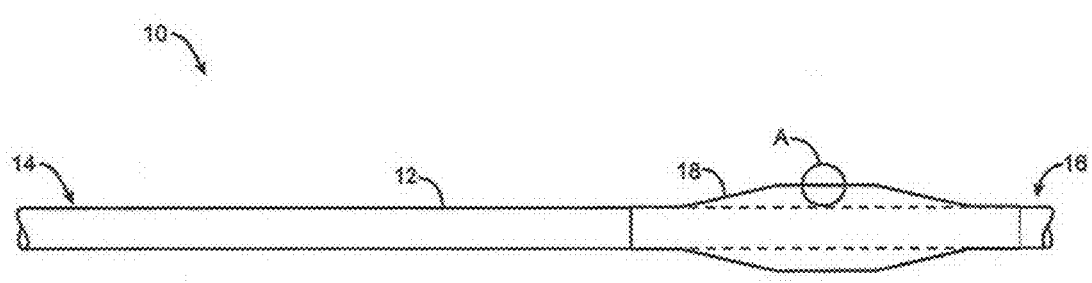
FIG. 1 is a schematic side view of a dilatation balloon catheter according to an embodiment of the present disclosure.

It is desirable to improve the flexibility and trackability of dilatation balloons while maintaining a high degree of strength in the balloon. Preferably, these improvements are made while using plasticizers, but limiting their ability to migrate out of the balloon. Improved flexibility and trackability would allow a surgeon to maneuver the balloon, and alternatively, a balloon and stent, through very small diameter vasculature that may have a large degree of blockage or plaque build-up. The high degree of strength provides the surgeon with maximum flexibility to inflate the balloon, and alternatively, to deliver a stent upon inflation, without bursting the balloon.

The term "plasticizer" is used herein to mean a material that can decrease the flexural modulus and/or tensile modulus of a polymer. The plasticizer may influence the morphology of the polymer and/or may affect (e.g., decrease) the melting temperature and/or glass transition temperature.

The term "nylon" is used herein to mean a linear polymer with at least one amide bond in the main chain. Thus, as used herein, "nylon" refers to homopolymers or copolymers of various types of nylon, optionally copolymerized with polymers other than nylon (e.g., polyether, polyurethane, polyester, polysiloxane, and the like). This includes diblock, triblock, segmented block copolymers including nylon.

Although various theories, such as the solubility parameter theory, can provide guidance for the development of plasticizers, it remains a trial-and-error process in actual practice. It is particularly difficult to find effective plasticizers for crystalline polymers. For example, Nylon-12 is a crystalline polymer. There are only a few plasticizers that are effective, with the most effective being the family of benzenesulfone amide compounds such as N-butylbenzensulfonamide.

In order to improve the flexibility of nylon-containing balloons with the use of one or more plasticizer(s), the plasticizer used is an amide-containing plasticizer selected from a compound having the following structural formulas:

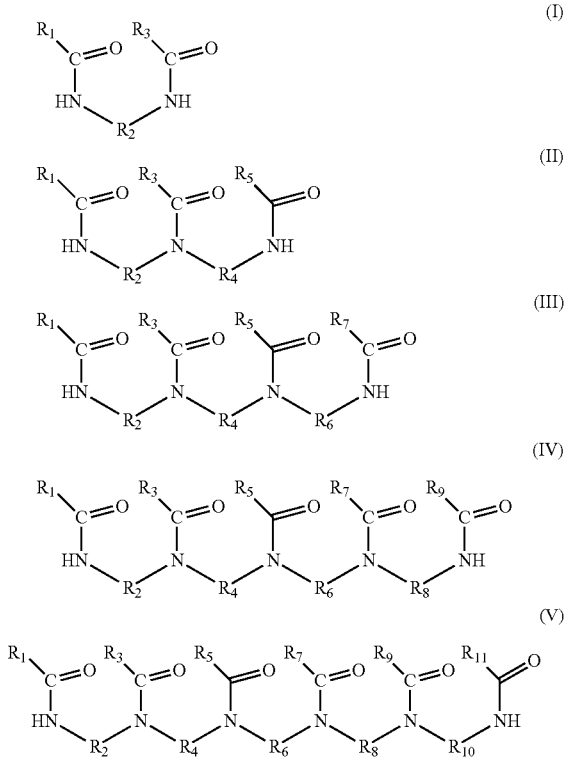

and combinations thereof wherein:

each of $R_1$, $R_3$, $R_5$, $R_7$, $R_9$, and $R_{11}$ is independently selected from a C2-C18 linear, branched, or cyclic monovalent aliphatic group (preferably, an alkyl group), optionally including unsaturation and/or functional groups of amide, ester, hydroxyl, phosphate groups, or combinations thereof, a C5-C12 monovalent aromatic group, and combinations thereof and each of $R_2$, $R_4$, $R_6$, $R_8$, and $R_{10}$ is independently selected from a C2-C18 linear, branched, or cyclic divalent aliphatic group (preferably, an alkylene group), optionally including unsaturation and/or functional groups of amide, ester, hydroxyl, phosphate groups, or combinations thereof, a C5-C12 divalent aromatic group, and combinations thereof.

In certain embodiments, the plasticizer is

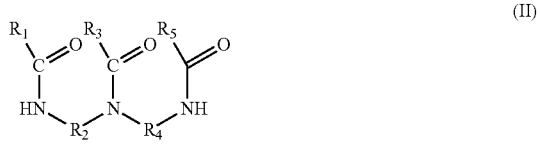

wherein:

each $R_1$, $R_3$, and $R_5$ is independently selected from a C2-C18 linear, branched, or cyclic alkyl group, a C5-C12 monovalent aromatic group, and combinations thereof; and each $R_2$ and $R_4$ is independently selected from a C1-C5 linear alkylene group, a C5-C12 divalent aromatic group, and combinations thereof.

In certain embodiments of the plasticizers of structural formulas (I) through (V), each $R_1$, $R_3$, $R_5$, $R_7$, $R_9$, and $R_{11}$ is independently selected from a C6-C12 linear, branched, or cyclic alkyl group. In certain embodiments, each $R_1$, $R_3$, $R_5$, $R_7$, $R_9$, and $R_{11}$ is independently selected from a C7-C8 linear, branched, or cyclic alkyl group. In certain embodiments, each $R_1$, $R_3$, $R_5$, $R_7$, $R_9$, and $R_{11}$ is independently selected from a linear alkyl group.

In certain embodiments of the plasticizers of structural formulas (I) through (V), each $R_2$, $R_4$, $R_6$, $R_8$, and $R_{10}$ is independently selected from a C2-C4 linear, branched, or cyclic alkylene group. In certain embodiments, each $R_2$, $R_4$, $R_6$, $R_8$, and $R_{10}$ is independently selected from a linear alkylene group.

In certain embodiments, each $R_1$, $R_3$, $R_5$, $R_7$, $R_9$, and $R_{11}$ can include aromatic groups, or combinations of aromatic and aliphatic groups. Examples include phenyl, tolyl, and benzyl groups.

In certain embodiments, each $R_1$, $R_3$, $R_5$, $R_7$, $R_9$, and $R_{11}$ optionally includes unsaturation in the monofunctional aliphatic groups. Examples of such groups include the following:

Myristoleic acid residual group $CH_3(CH_2)_3CH{=}CH(CH_2)_7{-}$

Oleic acid residual group cis-$CH_3(CH_2)_7CH{=}CH(CH_2)_7{-}$

Elaidic acid residual group trans-$CH_3(CH_2)_7CH{=}CH(CH_2)_7{-}$

Vaccenic acid residual group $CH_3(CH_2)_5CH{=}CH(CH_2)_9{-}$

In certain embodiments of the plasticizers of structural formulas (I) through (V), each $R_1$, $R_3$, $R_5$, $R_7$, $R_9$, and $R_{11}$ optionally includes functional groups of amide, ester, hydroxyl, phosphate groups, or combinations thereof in the monofunctional aliphatic groups (particularly, the alkyl groups). Examples of such groups are illustrated below.

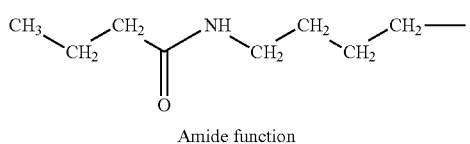

Amide function

-continued

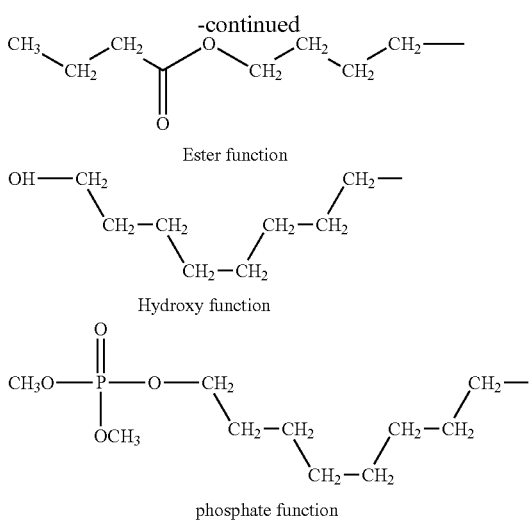

Ester function

Hydroxy function phosphate function

In certain embodiments of the plasticizers of structural formulas (I) through (V), each $R_2$, $R_4$, $R_6$, $R_8$, and $R_{10}$ optionally includes unsaturation in the difunctional groups. Examples of such groups are illustrated below.

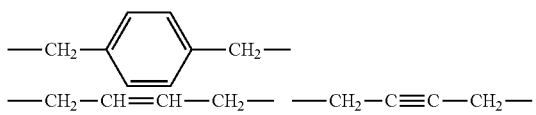

In certain embodiments, each $R_2$, $R_4$, $R_6$, $R_8$, and $R_{10}$ optionally includes functional groups of amide, ester, hydroxyl, phosphate groups, or combinations thereof in the difunctional aliphatic groups (particularly, the alkylene groups). Examples of such groups are illustrated below.

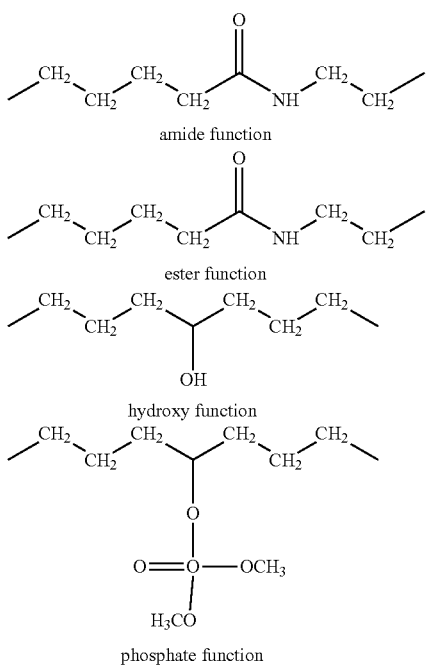

amide function ester function hydroxy function phosphate function

In certain embodiments, the plasticizer is a non-sulfur-containing amide-containing compound (i.e., an amide-containing compound that does not include sulfur).

Amide-containing plasticizers of the present disclosure can be prepared using a variety of synthetic procedures. For example, the amide-containing plasticizer can be prepared from an amine and a fatty acid in a stoichiometric amount.

In certain embodiments, amide-containing plasticizers of the present disclosure can be prepared from a direct amidation reaction with an amine and a carboxylic acid with or without a catalyst, such as boric acid, toluene sulfonic acid, phosphoric acid, etc. Typically, this is done using a stoichiometric amount or slight excess of these components, using stepwise addition or batch addition. The reaction can be carried out neat at high temperature (e.g., 100-350° C.), or in a solvent such as refluxing toluene, to remove water to drive the reaction to completion. For example, octanoic acid, heptanoic acid, nonanoic acid, lauric acid, 2-ethylhexanoic acid, or combinations thereof can be reacted with ethylenediamine to make compounds of Formula (I), or with diethylenetriamine or bis(2-aminopropyl)amine to make compounds of Formula (II), or with triethylenetetramine to make compounds of Formula (III), or with tetraethylenepentamine to make compounds of Formula (IV), or with pentaethylenehexamine to make compounds of Formula (V). Mixtures of various acids and/or mixtures of amines can be used as desired.

As known to those skilled in the art, they can also be synthesized from amines and carboxylic acid esters neat, or in a solvent, with or without a catalyst. Examples include amidation of ethylenediamine, or diethylenetriamine, or triethylenetetraamine with the methyl ester of lauric acid at 160-250° C. with or without 0.1 to 1% phosphoric acid or boric acid compounds in a pressurized vessel. Alternatively, these reactions can be carried out in a refluxing solvent, such as toluene or xylene.

Another method includes reaction of an amine compound with carboxylic acid anhydride or acid chloride, with or without a catalyst. Examples include ethylenediamine, diethylenetriamine, or triethylenetetraamine with 3 equivalents n-octanoic anhydride or n-octanoyl chloride at room temperature in a solvent such as THF and triethylamine.

An amide compound can also be prepared by Beckmann rearrangement with a catalyst such as sulfuric acid, etc.

All these reactions may not generate 100% pure product. The plasticizer can be purified by processes such as precipitation, recrystallization, extraction, column chromatography and vacuum, etc. as illustrated by Example 13. However, the plasticizers of the present disclosure can be used in the unpurified form, if desired.

In certain embodiments, the nylon is selected from the group of Nylon-6, Nylon-7, Nylon-8, Nylon-9, Nylon-10, Nylon-11, Nylon-12, Nylon-13, Nylon-14, Nylon-15, Nylon-16, Nylon-17, Nylon-18, Nylon-6,6, Nylon-6,8, Nylon-6,10, Nylon-6,12, Nylon-6,14, Nylon-8,8, Nylon-8,10, Nylon-8,12, Nylon-8,14, Nylon-10,10, Nylon-10,12, Nylon-8,12, Nylon-10,14, Nylon-12,12, Nylon-12,14, Nylon-14,16, and combinations thereof. In certain embodiments, the nylon is selected from the group of Nylon-6, Nylon-11, Nylon-12, Nylon-6,6, Nylon-6,10, and combinations thereof.

The nylon can be copolymerized with other polymers, such as polyether, for example. Block copolymers of the nylons such as polyether-co-Nylon 12 can be used if desired. The examples include PEBAX family of polymers with various polyether (poly(tetramethylene oxide)) compositions produced by Arkema Inc. Such examples include PEBAX 7233, PEBAX 7033, PEBAX 6333, PEBAX 4033, PEBAX 3533, PEBAX 2533, etc. Other examples of nylon-including polymers, which is within the scope of "nylon" as used herein, include polyurethane-block-nylon, polyester-block-nylon, polysiloxane-block-nylon.

Thus, as used herein, "nylon" refers to homopolymers or copolymers of various types of nylon, optionally copolymerized with polymers other than nylon (e.g., polyether, polyurethane, polyester, polysiloxane, and the like). This includes diblock, triblock, segmented block copolymers including nylon.

In certain embodiments, the nylon is Nylon-12.

Preferably, the number average molecular weight of the nylon may be at least 5,000 Daltons, and preferably no more than 5,000,000 Daltons. In the case of nylon block copolymers, the non-nylon block has a number average molecular weight between 500 to 1,000,000 Daltons.

The nylon and amide-containing plasticizer can be combined using a variety of techniques including, for example, compounded in a mixer such as an extrusion machine, above the melting point or glass transition temperature. As illustrated by Example 2, Nylon-12 can be compounded with 5-10 wt-% N,N',N"-trioctanoyl diethyelenetriamine in a Brabender mixer at 210° C. As illustrated by Example 9, Nylon-12 can be compounded with 10 wt-% of the same plasticizer with an extruder at 210° C.

In certain embodiments, the plasticized nylon of the present disclosure includes the amide-containing plasticizer in an amount of at least 0.1 wt-%, at least 1 wt-%, at least 5 wt-%, at least 10 wt-%, or at least 15 wt-%, based on the total weight of the plasticized nylon.

In certain embodiments, the plasticized nylon of the present disclosure includes the amide-containing plasticizer in an amount of up to 50 wt-%, or up to 60 wt-%, or up to 70 wt-%, based on the total weight of the plasticized nylon. Herein, "up to" a particular number includes the number.

The thermal and mechanical analysis of the compounded resins (plasticized nylon) showed effectiveness of the plasticizer as illustrated by a large number of examples (e.g., Examples 1, 12, 19, and 24). The results of Example 24 are of particular interest. Within the range of 5 to 10 wt-% of plasticizer, the plasticized polymers retained the tensile strength of the base material (Nylon-12), while the modulus decreased with increasing plasticizer level. Using Nylon-12 with a different molecular weight (e.g., GRILAMID L25) this feature was further confirmed (Example 12). This means the material became softer while its mechanical strength was maintained. This is very desirable for applications such as angioplasty balloons. The high strength is desirable for high burst pressure and low profile, while the high flexibility is desirable for deliverability.

Another feature of the plasticizer is its compatibility with E-beam sterilization, which is typically used in the manufacture of medical devices. As illustrated in Example 3, the compounded resin showed no change of mechanical properties after 40 kGy E-beam radiation.

Yet, another advantage of the disclosed plasticizer is their low volatility. Plasticizers described in the Example Section showed practically no weight loss at 100° C. under high vacuum after drying. Thus, when the compound resin is processed there is little or no loss of plasticizer at high temperature. This is also an advantage for durability of the plasticization effect, as preferably there is no loss of plasticizer during processing and use.

The plasticized nylon of the present disclosure may include one or more additives. The term "additive" is used herein to refer to any material added to the polymer to affect the polymer's (e.g., balloon's) properties. Examples of additives for use in the disclosure include fillers such as tungsten, barium sulfate, bismuth subcarbonate and inorganic nanoparticles, antioxidants, (e.g., phenolic antioxidants such as BHT and IRGANOX 1098), colorants, crosslinking agents, impact strength modifiers, and combinations thereof.

The plasticized nylon of the present disclosure can be used in a variety of medical devices or portions thereof. Examples include, but are not limited to, a dilatation balloon, stent delivery balloon, positioning balloon, diagnostic balloon, occlusion balloon, multifunctional balloon, multi-lumen balloon, cryoballoon, light therapy balloon, ablation balloons including AF and renal denervation balloon, heat transfer balloon, inner member, distal tip, medical tubing, or a catheter. Other medical devices include structural heart devices, orthopedic and spinal devices, drug delivery devices include insulin pump, neural devices, pacemaker, implantable cardioverter defibrillator, surgery devices, pulmonary devices, thrombus removal devices, endoscope devices, etc.

In certain embodiments, the plasticized nylon is used in a balloon or medical tubing. In certain embodiments, the plasticized nylon is used in a balloon or catheter.

In one embodiment, the present disclosure provides a dilatation balloon catheter that includes: a tubular elongated catheter shaft having proximal and distal portions; and a dilatation balloon disposed on said shaft, wherein the shaft and/or balloon includes a plasticized nylon of the present disclosure.

Turning to the figures, a dilatation balloon catheter 10 (herein also referred to as "catheter") according to an embodiment of the disclosure is illustrated in FIG. 1. As illustrated, the catheter 10 includes a tubular elongated catheter shaft 12 (herein also referred to as "catheter shaft" or "shaft") having a proximal portion 14 and a distal portion 16, and a dilatation balloon 18 disposed on or otherwise connected to the distal portion 16 of the shaft 12. The balloon 18 can have a wall (a portion of which is designated by "A") that includes a single layer or dual layer of polymeric materials, for example. The wall can include therapeutic agents or biologically active materials (e.g., antiproliferative agents such as rapamycin and its derivatives, paclitaxel and its derivatives, anti-inflamatory agents, and anti-thrombogenic agents) disposed thereon, optionally with one or more other additives or polymeric coatings.

Dilatation is used herein to refer to the expandability of the balloon. In certain embodiments, balloons of the present disclosure are expandable 2% to 40% greater than the original balloon size. Preferably, the expandability of the balloon is in the range of 5% to 20%.

Figure 2:
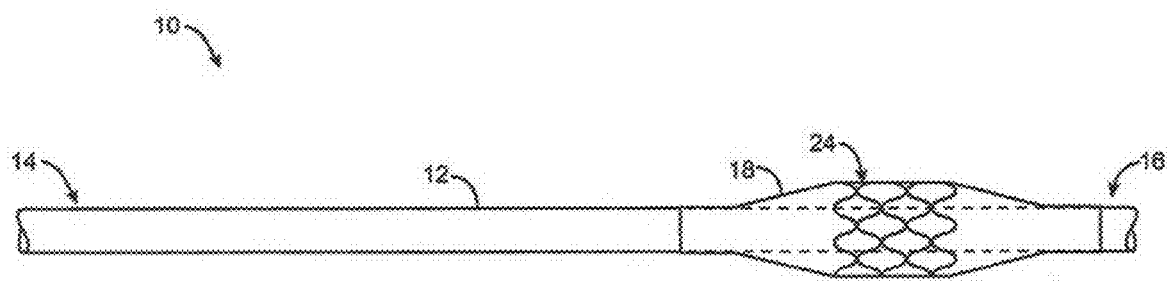
FIG. 2 is a schematic side view of a stent delivery catheter according to another embodiment of the present disclosure.

With reference to FIG. 2, a balloon 18 of the present disclosure can optionally further include a stent 24 disposed on the balloon 18. The balloon 18 may have high hoop strengths and allow for expanded delivery of the stent upon inflation of the balloon without bursting or puncturing the balloon. The stent 24 optionally includes a therapeutic agent or biologically active material. Any therapeutic agent or biologically active material, as described above, can be used in the stent. Specific examples include, but are not limited to, corticosteroids, such as dexamethasone, immunosuppressants, such as everolimus, sirolimus, and tacrolimus, zotarolimus, and chemotherapeutic agents, such as paclitaxel. The therapeutic agent or biologically active material elutes out of the stent and into the surrounding tissue over a controlled and predictable time.

Figure 6:
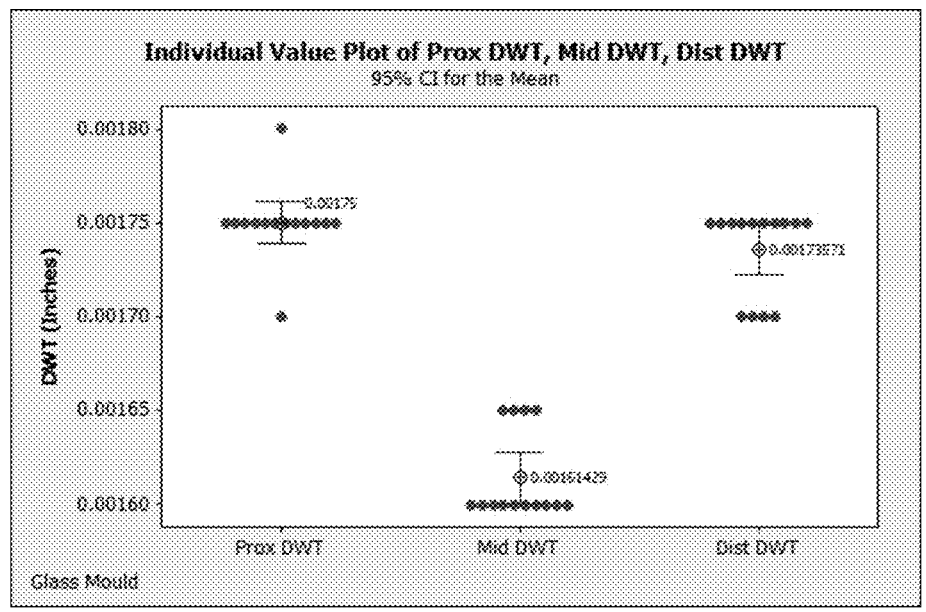
FIG. 6 is a graph of balloon double wall thickness (Example 11)

As illustrated in Example 11, 3×18 mm balloons were manufactured in a glass or stainless balloon mold from tubings made in Example 10. The balloons had very thin double wall thickness (DWT) at locations of proximal (Prox), middle (Mid), and distal (Dis) portions as shown in FIG. 6. The average burst pressure of 22.3 atmospheres (atm) was quite high for such a thin balloon. This is because the plasticized material maintained the tensile strength of the base material. Due to lower modulus and thinner DWT the balloon also showed excellent flexibility on the finished device (crimped with 3×18 mm Integrity Stent) according to 2D-tracking and 90 degree tracking tests that simulate tortuous blood vessel anatomy. The 90-degree tracking force was 259 gf (average of 10) compared to 439 gf (average of 10) on a commercial product. The 2D tracking maximum force on the 4th push was 106 gf (average of 10) compared with 219 gf (average of 10) of a commercial product.

As those skilled in the art will appreciate, the plasticizers disclosed herein are also very useful beyond medical applications, based upon the data presented. The non-medical applications of such materials include, but are not limited to, fuel line, tubing for hydraulic clutches, vacuum line, tubing for diesel fuel lines permanently exposed to high temperature, extrusion coating for metal tubing, air brake tubing, sheath of electric cable, flexible tubing for pneumatic systems, electrical wire insulation, quick disconnectors, precision molding parts with isotropic shrinkages, sports wear, etc.

Illustrative Embodiments

1. A medical device comprising a plasticized nylon, wherein the plasticized nylon comprises a nylon and an amide-containing plasticizer selected from a compound having the following structural formulas:

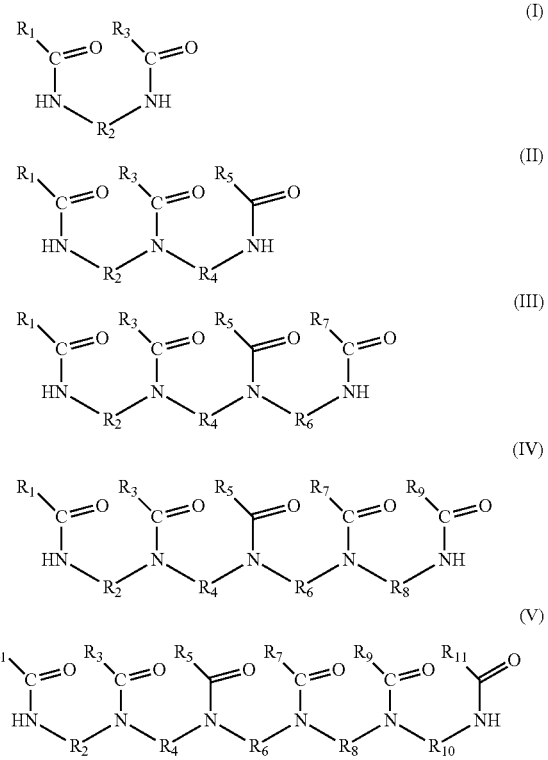

and combinations thereof;

wherein:
each $R_1$, $R_3$, $R_5$, $R_7$, $R_9$, and $R_{11}$ is independently selected from a C2-C18 linear, branched, or cyclic monovalent aliphatic group, a C5-C12 monovalent aromatic group, and combinations thereof; and
each $R_2$, $R_4$, $R_6$, $R_8$, and $R_{10}$ is independently selected from a C2-C18 linear, branched, or cyclic divalent aliphatic group, a C5-C12 divalent aromatic group, and combinations thereof.

2. The medical device of embodiment 1 wherein each $R_1$, $R_3$, $R_5$, $R_7$, $R_9$, and $R_{11}$ is independently selected from a C6-C12 linear, branched, or cyclic alkyl group.
3. The medical device of embodiment 2 wherein each $R_1$, $R_3$, $R_5$, $R_7$, $R_9$, and $R_{11}$ is independently selected from a C7-C8 linear, branched, or cyclic alkyl group.
4. The medical device of any of embodiments 1 through 3 wherein each $R_1$, $R_3$, $R_5$, $R_7$, $R_9$, and $R_{11}$ is independently selected from a linear alkyl group.
5. The medical device of any of embodiments 1 through 4 wherein each $R_2$, $R_4$, $R_6$, $R_8$, and $R_{10}$ is independently selected from a C2-C4 linear, branched, or cyclic alkylene group.
6. The medical device of any of embodiments 1 through 5 wherein each $R_2$, $R_4$, $R_6$, $R_8$, and $R_{10}$ is independently selected from a linear alkylene group.
7. The medical device of any of embodiments 1 through 6 wherein the plasticizer has the following structural formula:

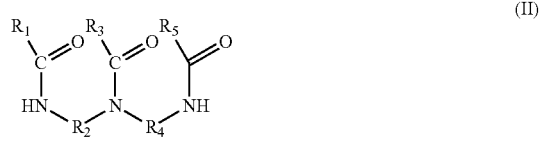

wherein:
each $R_1$, $R_3$, and $R_5$ is independently selected from a C2-C18 linear, branched, or cyclic alkyl group, a C5-C12 monovalent aromatic group, and combinations thereof and
each $R_2$ and $R_4$ is independently selected from a C1-C5 linear alkylene group, a C5-C12 divalent aromatic group, and combinations thereof.
8. The medical device of any of embodiments 1 through 7 wherein the nylon is selected from the group of Nylon-6, Nylon-7, Nylon-8, Nylon-9, Nylon-10, Nylon-11, Nylon-12, Nylon-13, Nylon-14, Nylon-15, Nylon-16, Nylon-17, Nylon-18, Nylon-6,6, Nylon-6,8, Nylon-6,10, Nylon-6,12, Nylon-6,14, Nylon-8,8, Nylon-8,10, Nylon-8,12, Nylon-8,14, Nylon-10,10, Nylon-10,12, Nylon-8,12, Nylon-10,14, Nylon-12,12, Nylon-12,14, Nylon-14,16, and combinations thereof.
9. The medical device of embodiment 8 wherein the nylon is selected from the group of Nylon-6, Nylon-11, Nylon-12, Nylon-6,6, Nylon-6,10, and combinations thereof.
10. The medical device of embodiment 9 wherein the nylon is Nylon-12.
11. The medical device of any of embodiments 1 through 10 wherein the amide-containing plasticizer is present in an amount of at least 0.1 wt-%, based on the total weight of the plasticized nylon.
12. The medical device of any of embodiments 1 through 11 wherein the amide-containing plasticizer is present in an amount of up to 50 wt-%, based on the total weight of the plasticized nylon.

13. The medical device of any of embodiments 1 through 12 wherein the amide-containing plasticizer is prepared from an amine and a fatty acid in a stoichiometric amount.

14. A medical device comprising a plasticized nylon, wherein the plasticized nylon comprises Nylon-12 and an amide-containing plasticizer having the following structural formula:

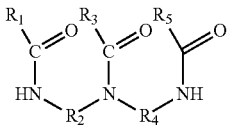
(II)

wherein:

each $R_1$, $R_3$, and $R_5$ is independently selected from a C2-C18 linear, branched, or cyclic alkyl group, a C5-C12 monovalent aromatic group, and combinations thereof; and each $R_2$ and $R_4$ is independently selected from a C1-C5 linear alkylene group, a C5-C12 divalent aromatic group, and combinations thereof.

15. The medical device of any of embodiments 1 through 14 wherein the plasticized nylon further comprises at least one of a filler, antioxidant, colorant, crosslinking agent, impact strength modifier, or combinations thereof.

16. The medical device of any of embodiments 1 through 15 which is a balloon or medical tubing.

17. The medical device of embodiment 16 which is a balloon or catheter.

18. A balloon dilatation catheter, comprising:

a tubular elongated catheter shaft having proximal and distal portions; and a dilatation balloon disposed on said shaft, wherein the shaft and/or balloon comprises a plasticized nylon, wherein the plasticized nylon comprises Nylon-12 and an amide-containing plasticizer having the structural formula:

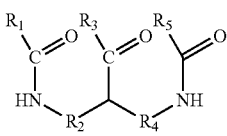
(II)

wherein:

each $R_1$, $R_3$, and $R_5$ is independently selected from a C2-C18 linear, branched, or cyclic alkyl group, a C5-C12 monovalent aromatic group, and combinations thereof; and each $R_2$ and $R_4$ is independently selected from a C1-C5 linear alkylene group, a C5-C12 divalent aromatic group, and combinations thereof.

19. The catheter of embodiment 18 further comprising a stent disposed on the balloon.

20. A plasticized nylon comprising nylon and an amide-containing plasticizer selected from a compound having the following structural formulas:

(I)

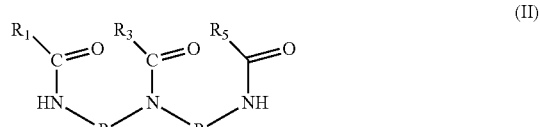
(II)

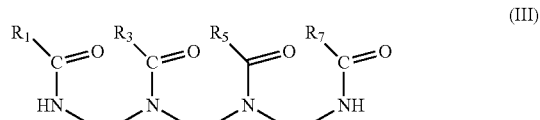
(III)

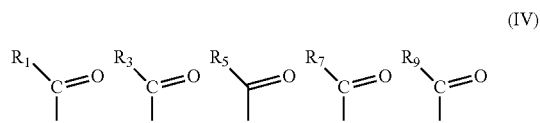
(IV)

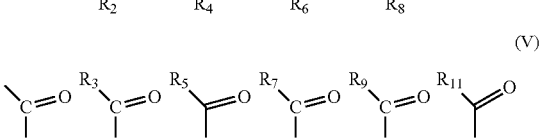
(V)

and combinations thereof;

wherein:

each $R_1$, $R_3$, $R_5$, $R_7$, $R_9$, and $R_{11}$ is independently selected from a C2-C18 linear, branched, or cyclic monovalent aliphatic group, a C5-C12 monovalent aromatic group, and combinations thereof; and each $R_2$, $R_4$, $R_6$, $R_8$, and $R_{10}$ is independently selected from a C2-C18 linear, branched, or cyclic divalent aliphatic group, a C5-C12 divalent aromatic group, and combinations thereof.

21. The plasticized nylon of embodiment 20 wherein each $R_1$, $R_3$, $R_5$, $R_7$, $R_9$, and $R_{11}$ is independently selected from a C6-C12 linear, branched, or cyclic alkyl group.

22. The plasticized nylon of embodiment 21 wherein each $R_1$, $R_3$, $R_5$, $R_7$, $R_9$, and $R_{11}$ is independently selected from a C7-C8 linear, branched, or cyclic alkyl group.

23. The plasticized nylon of any of embodiments 20 through 22 wherein each $R_1$, $R_3$, $R_5$, $R_7$, $R_9$, and $R_{11}$ is independently selected from a linear alkyl group.

24. The plasticized nylon of any of embodiments 20 through 23 wherein each $R_2$, $R_4$, $R_6$, $R_8$, and $R_{10}$ is independently selected from a C2-C4 linear, branched, or cyclic alkylene group.

25. The plasticized nylon of embodiment 24 wherein each $R_2$, $R_4$, $R_6$, $R_8$, and $R_{10}$ is independently selected from a linear alkylene group.

26. The plasticized nylon of any of embodiments 20 through 25 wherein the plasticizer has the following structural formula:

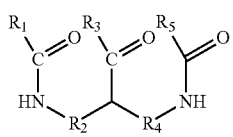

(II)

wherein:
each $R_1$, $R_3$, and $R_5$ is independently selected from a C2-C18 linear, branched, or cyclic alkyl group, a C5-C12 monovalent aromatic group, and combinations thereof and
each $R_2$ and $R_4$ is independently selected from a C1-C5 linear alkylene group, a C5-C12 divalent aromatic group, and combinations thereof.

27. The plasticized nylon of any of embodiments 20 through 26 wherein the nylon is selected from the group of Nylon-6, Nylon-7, Nylon-8, Nylon-9, Nylon-10, Nylon-11, Nylon-12, Nylon-13, Nylon-14, Nylon-15, Nylon-16, Nylon-17, Nylon-18, Nylon-6,6, Nylon-6,8, Nylon-6,10, Nylon-6,12, Nylon-6,14, Nylon-8,8, Nylon-8,10, Nylon-8,12, Nylon-8,14, Nylon-10,10, Nylon-10,12, Nylon-8,12, Nylon-10,14, Nylon-12,12, Nylon-12,14, Nylon-14,16, and combinations thereof.

28. The plasticized nylon of embodiment 27 wherein the nylon is selected from the group of Nylon-6, Nylon-11, Nylon-12, Nylon-6,6, Nylon-6,10, and combinations thereof.

29. The plasticized nylon of embodiment 28 wherein the nylon is Nylon-12.

30. The plasticized nylon of any of embodiments 20 through 29 comprising 0.1 wt-% to 50 wt-% of the amide-containing plasticizer.

31. The plasticized nylon of any of embodiments 20 through 30 wherein the amide-containing plasticizer is prepared from an amine and a fatty acid in a stoichiometric amount.

32. The plasticized nylon of any of embodiments 20 through 31 wherein the plasticized nylon further comprises at least one of a filler, antioxidant, colorant, crosslinking agent, impact strength modifier, or combinations thereof.

EXAMPLES

Example 1

Synthesis of the Plasticizer N,N',N"-trioctanoyl diethylenetriamine

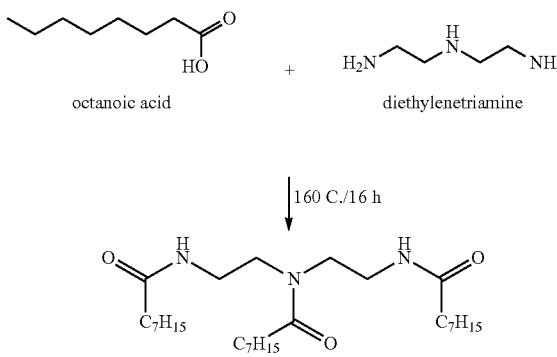

A sample of 6.88 grams (g) of diethyletriamine was gradually added to 30.0 g of octanoic acid in a glass bottle. A spin bar was added to the bottle, which was sealed and purged with nitrogen. The contents were heated at 160° C. while being purged with nitrogen overnight on an oil batch. The product from the reaction was further dried at 100° C. with a vacuum oven overnight.

Example 2

Compounding Plasticizer with Nylon-12

Figure 3:
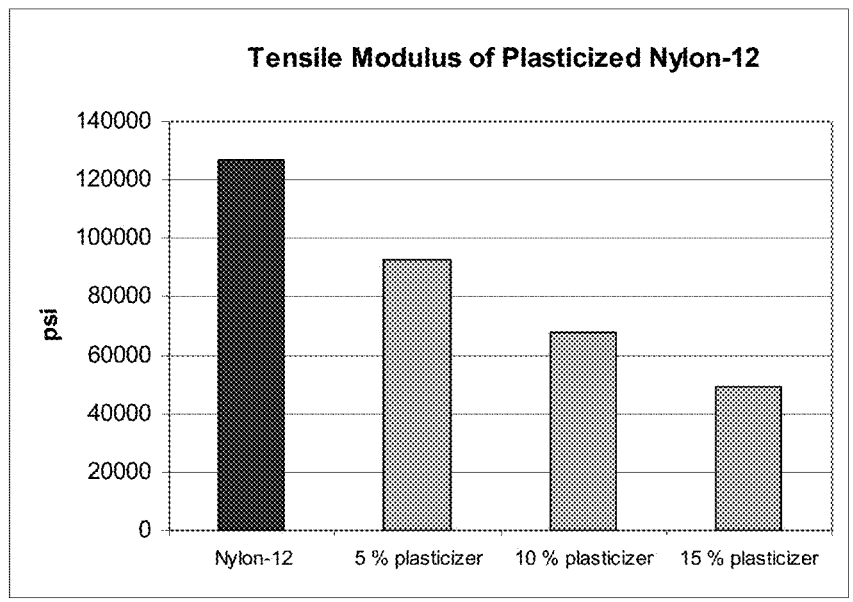
FIG. 3 is a graph of tensile modulus of an exemplary plasticized Nylon-12 (Example 2)
Figure 4:
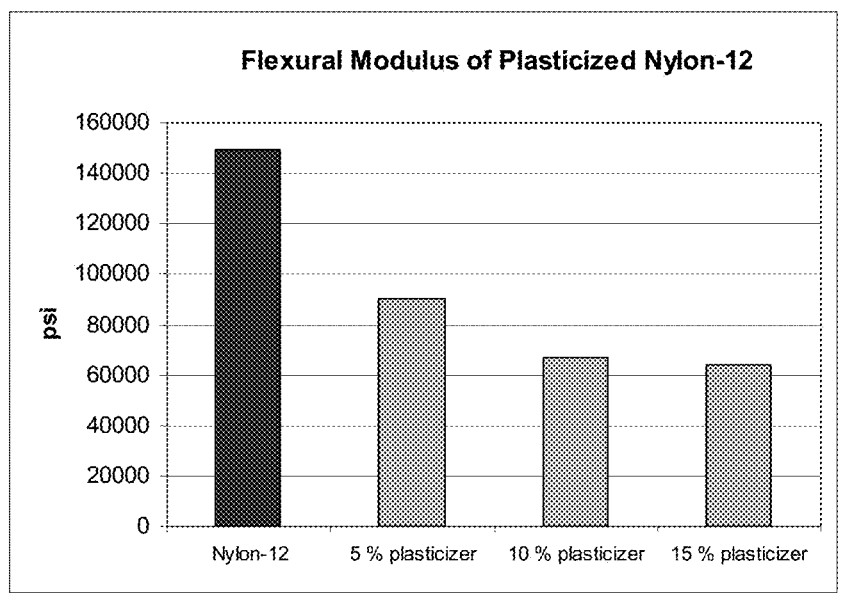
FIG. 4 is a graph of flexural modulus of an exemplary plasticized Nylon-12 (Example 2)

Samples of 5, 10, and 15 wt-% of plasticizer from Example 1 were compounded with Nylon-12 in a Brabender mixer at 210° C. Sheets (30-mils thick) were pressed at 200° C. Tensile specimens were punched and tested on an INSTRON testing machine at a cross-head speed of 2 inches/minute according to ASTM D638 test Method. The flexural properties were tested according to ASTM D790-97B test method. Melting point and crystallinity of the plasticized Nylon-12 as determined by DSC are shown in Table 1. The average tensile and flexural moduli of plasticized Nylon-12 are shown in FIG. 3 and FIG. 4, respectively.

TABLE 1

Thermal Properties of Plasticized Nylon-12

| DSC Results | Nylon-12 (base material) | 5% plasticizer | 10% plasticizer | 15% plasticizer |
|---|---|---|---|---|
| $T_m$ Melt peak(° C.) | 177.7 | 176.6 | 175.9 | 173.9 |
| $\Delta H_m$ (J/g) | 67.6 | 60.2 | 58.2 | 54.7 |
| % Crystallinity | 32.3 | 28.8 | 27.8 | 26.2 |

Both flexural and tensile moduli of Nylon-12 decreased after adding the plasticizer. The melting and the crystallinity were depressed. The results suggest this compound is an effective plasticizer.

Example 3

E-Beam Sterilization of Plasticized Nylon

Figure 5:
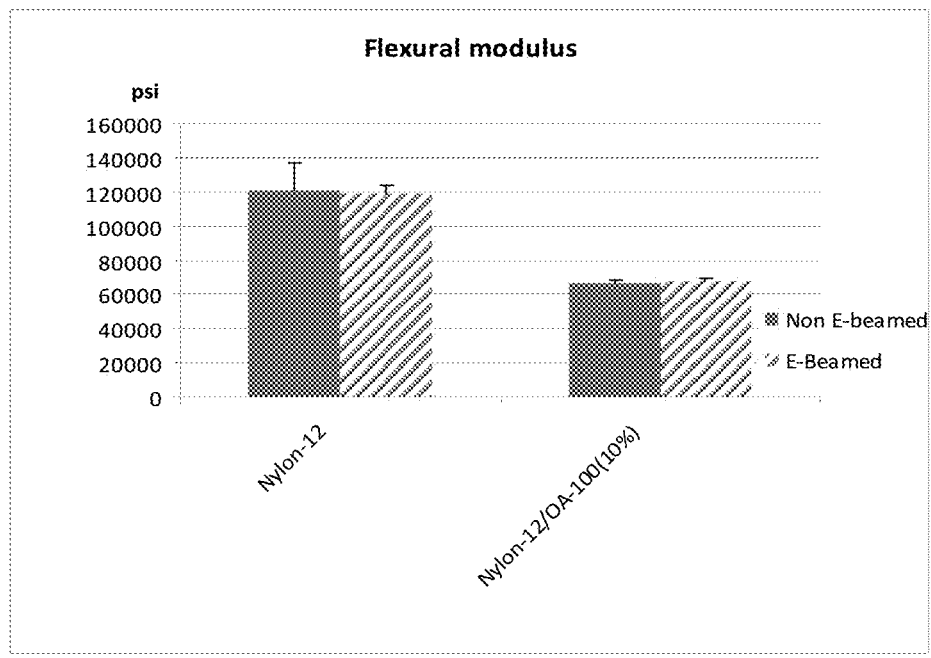
FIG. 5 is a graph of the flexural modulus of an exemplary plasticized Nylon-12 before and after E-beam sterilization (Example 3)

The film material with 10 wt-% plasticizer from Example 2 was subjected to 40 kGy dosage of E-beam radiation. The flexural modulus did not change, indicating the material is compatible with E-beam sterilization (FIG. 5).

Example 4

Synthesis of the Plasticizer N,N',N"-triheptanoyl diethylenetriamine

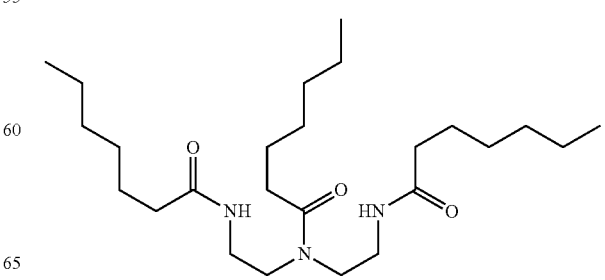

A sample of 7.62 g of diethylenetriamine was gradually added to 30.0 g of heptanoic acid in a glass bottle. A spin bar was added to the bottle, which was sealed and purged with nitrogen. The contents were heated at 160° C. while being purged with nitrogen overnight on an oil batch. The product from the reaction was further dried at 100° C. with a vacuum oven overnight.

Example 5

Synthesis of N,N',N''-trinonanoyl diethylenetriamine

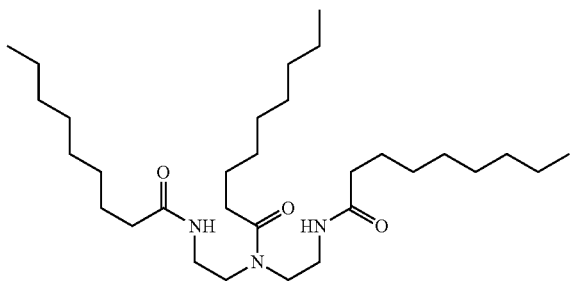 [SMILES: CCCCCCCCC(=O)NCCN(CCNC(=O)CCCCCCCC)C(=O)CCCCCCCC]

A sample of 6.27 g of diethylenetriamine was gradually added to 30.0 g of nonanoic acid in a glass bottle. A spin bar was added to the bottle, which was sealed and purged with nitrogen. The contents were heated at 160° C. while being purged with nitrogen overnight on an oil batch. The product from the reaction was further dried at 100° C. with a vacuum oven overnight.

Example 6

Synthesis of the Diethylenetriamine Triamide with Mixed Chain Length

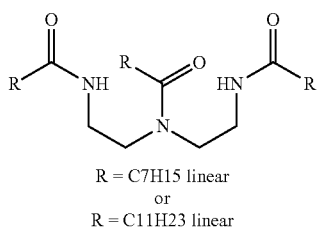

R = C7H15 linear
or
R = C11H23 linear

A sample of 6.10 g of diethylenetriamine was gradually added to 15.0 g of octanoic acid and 15.0 g of lauric acid in a glass bottle. A spin bar was added to the bottle, which was sealed and purged with nitrogen. The contents were heated at 160° C. while being purged with nitrogen overnight on an oil batch. The product from the reaction was further dried at 100° C. with a vacuum oven overnight.

Example 7

Synthesis of the Plasticizer with Branched Chain

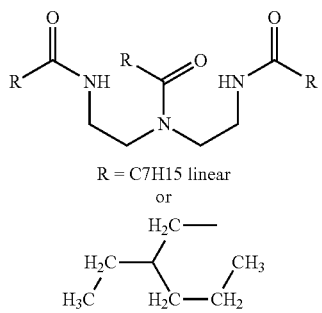

R = C7H15 linear
or
$H_2C-$
$H_2C-$ $CH_3$
$H_3C$ $H_2C-CH_2$

A sample of 6.88 g of diethylenetriamine was gradually added to 6.0 g of 2-ethylhexanoic acid in a glass bottle. A spin bar was added to the bottle, which was sealed and purged with nitrogen. The contents were heated at 160° C. while being purged with nitrogen overnight on an oil batch. The bottle was opened and 24.0 g of octanoic acid was charged. The bottle was repurged with nitrogen, sealed and heated in a 160° C. oil bath overnight. The product from the reaction was further dried at 100° C. with a vacuum oven overnight.

Example 8

Synthesis of the Plasticizer N,N',N''-trioctanoyl diethylenetriamine

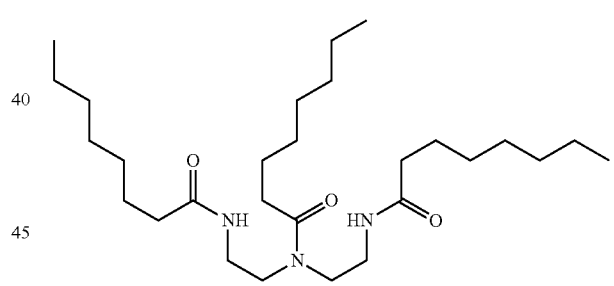

A four-neck 1-L reaction kettle equipped with a mechanical stirrer, nitrogen inlet/outlet, thermal couple and additional funnel was charged with 600 g of octanoic acid. A sample of 141.7 g of diethylenetriamine was added dropwise to the reactor while the exothermic reaction temperature was controlled below 80° C. under nitrogen purge. The additional funnel was replaced with a Dean-Stark trap fitted with a condenser. The reaction kettle was fitted with a heating mantel. The temperature was ramped to 150° C. The reaction is kept at 150° C. for one hour. The temperature was ramped to 200° C. The reaction was kept at 150° C. for one hour. The Dean-Stark trap and condenser were removed. The system remained purged with nitrogen until the vacuum is gradually applied to the maximum to remove water and excess octanoic acid. They were collected in a dry ice trap. The reaction remained at 200° C. under vacuum for two hours. The reaction was cooled down to 100° C. The product was transferred to a glass container while it was still in the liquid state.

Example 9

Compounding Plasticizer with Nylon-12

A sample of 40 lbs of Nylon-12 resin was dried three hours at 80° C. under vacuum. Plasticizer from Example 8 was melted in an oven at 110° C. and transferred to a reservoir where it was maintained at 120 C. Nylon-12 resin was metered from an Accurate Feeder and plasticizer was pumped to the first and second ports on the Buss extruder. The extruder was operated in a temperature range 200-220° C. The plasticizer level was increased to 10 wt-%. The Buss extruder was run at a screw speed of 240 revolutions per minute (rpm). Resin was metered at 47.52 grams per minute (g/min) and plasticizer at 5.28 g/min. About 2-mm strands were cooled in a water trough, chopped to a similar length and collected at a rate of 7 pounds per hour (lbs/hr). Product was collected continuously.

Example 10

Extrusion of Plasticized Nylon

The plasticizer compounded resin from Example 9 was extruded on Harrel extruder at approximately 400° F. to form tubings with an inside diameter of 0.0205 inch and an outside diameter of 0.0430 inch. The processing conditions were adjusted to achieve elongation of the tubing at 2.6 inches as tested on an INSTRON testing machine.

Example 11

Balloon Made From Plasticized Nylon

Balloons (3×18 mm) were manufactured in a glass or stainless balloon mold from tubings made in Example 10. The balloon had thin double wall thickness (DWT) as shown in FIG. 6 and high average burst pressure of 22.3 atm. The balloon also showed excellent flexibility on the finished device (crimped with 3×18 mm Integrity Stent) according to 2D-tracking and 90 degree tracking tests to simulate tortuous arterial anatomy. The 90 degree tracking force was 259 gf (average of 10) compared to 439 gf (average of 10) on a commercial product. The 2D tracking maximum force on the 4th push was 106 gf (average of 10) compared with 219 gf (average of 10) of a commercial product.

Example 12

Compounding Plasticizer with GRILAMID L25 Nylon-12

Figure 7:
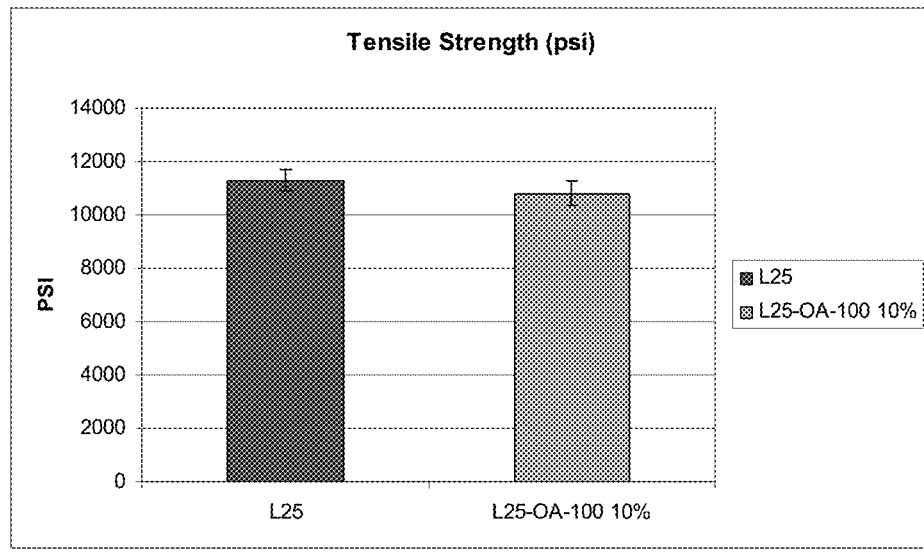
FIG. 7 is a graph of the tensile strength of an exemplary plasticized Nylon-12 (Example 12)
Figure 8:
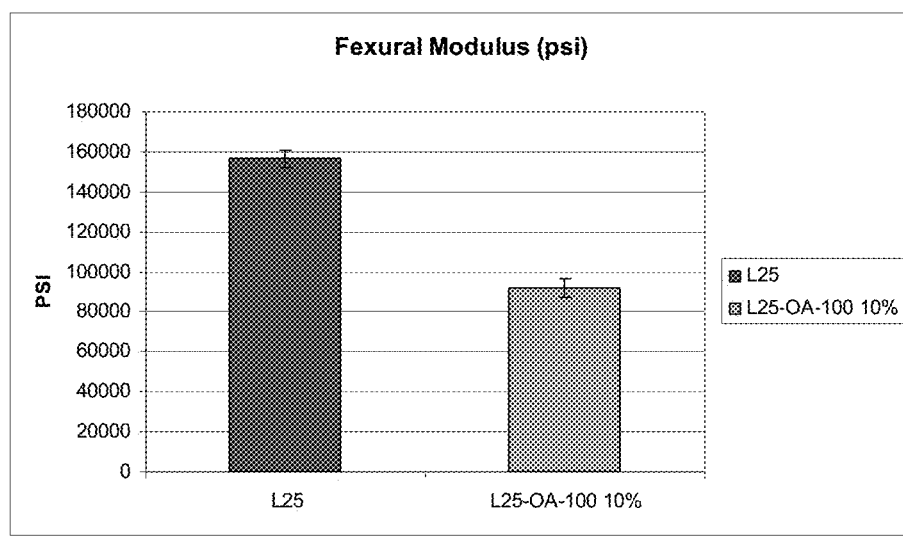
FIG. 8 is a graph of the flexural modulus of an exemplary plasticized Nylon-12 (Example 12)
Figure 9:
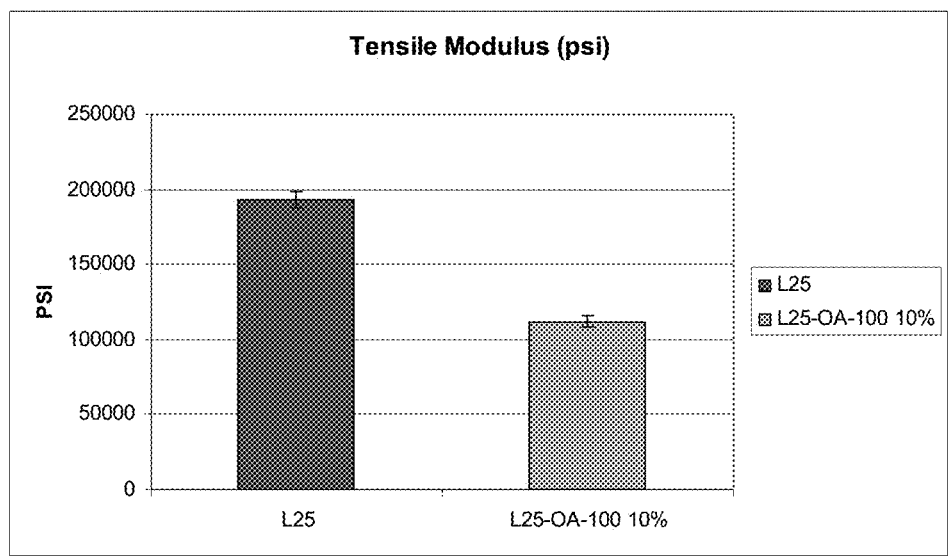
FIG. 9 is tensile modulus of an exemplary plasticized Nylon-12 (Example 12)

GRILAMID L25 (coded L25: Nylon-12 from EMS-Grivory) was compounded with plasticizer from Example 10 (coded OA-100) under similar conditions as described in Example 9. The mechanical properties of film pressed from the resin are shown in FIG. 7 (Tensile Strength), FIG. 8 (Flexural Modulus), and FIG. 9 (Tensile Modulus). The tensile strength of base resin GRILAMID L25 was maintained, while the flexural modulus decreased significantly after adding 10 wt-% of the plasticizer.

Example 13

Purification of N,N',N''-trioctanoyl diethylenetriamine

An unpurified sample (50 g) of material from Example 8 was dissolved in 100 mL methanol. The solution was precipitated in 700 mL 1% $Na_2CO_3$ aqueous solution. The solid was filtered and washed with deionized water and dried in vacuum. After crystallization in ethyl acetate twice, a pure white compound was obtained with mp of 97.9° C. (by DSC). Elemental analysis for $C_{28}H_{55}N_3O_3$: Calc. C, 69.81; H, 11.51; N, 8.72 Found: C, 69.92; H, 11.79; N, 8.69.

Example 14

Compounding Plasticizer with RILSAN Nylon-12

A sample of 10 wt-% of purified plasticizer from Example 13 was compounded with RILSAN Nylon-12 at 210° C. with a Barbender mixer. Films were pressed at 210° C. with the compounded resin. The mechanical properties of the resins using purified and unpurified plasticizer were similar. Flexural elastic modulus of 71839 pounds per square inch (psi) (purified material) was obtained vs 72345 psi (unpurified material), as well as tensile elastic modulus or 85644 psi (purified) was obtained vs 82997 psi (unpurified material).

Example 15

In Vitro Cytotoxicity Test

A 30-mil thick film (30 cm²) from Example 14 was extracted with 1×MEM (Minimal Essential Medium) along with negative and positive controls at 37° C. in the presence of $CO_2$ for 24-25 hours. Upon completion of the extraction, the test and control extracts were placed separately on triplicate confluent monomlayers of L-929 Mouse Fibroblast cells and then incubated in the presence of $CO_2$. The monolayers for the test extract, positive and negative controls, were graded microscopically after 24 and 48 hours of incubation. The test article had a grade of zero after 48 hours of incubation, thus deemed non-cytotoxicity in vitro.

Example 16

Synthesis of N-(2-aminoethyl)-1,3-propanediamine heptanoic acid triamide

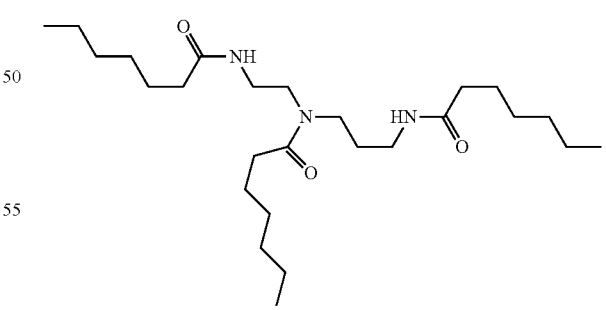

A sample of 8.66 g of N-(2-aminoethyl)-1,3-propanediamine was gradually added to 30.0 g of heptanoic acid in a glass bottle. A spin bar was added to the bottle, which was sealed and purged with nitrogen. The contents were heated at 160° C. while being purged with nitrogen overnight on an oil batch. The product from the reaction was further dried at 100° C. with a vacuum oven overnight.

Example 17

Synthesis of N-(2-aminoethyl)-1,3-propanediamine octanoic acid triamide

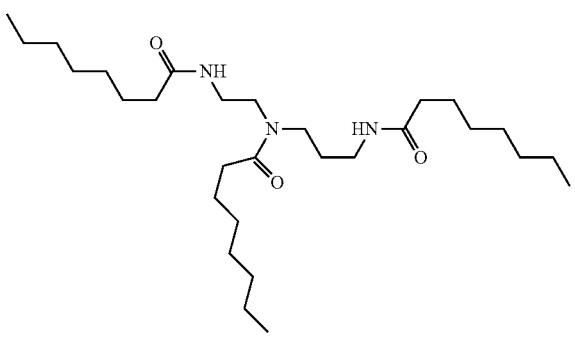 [SMILES: CCCCCCCC(=O)NCCCN(CCNC(=O)CCCCCCC)C(=O)CCCCCCC]

A sample of 7.82 g of N-(2-aminoethyl)-1,3-propanediamine was gradually added to 30.0 g of octanoic acid in a glass bottle. A spin bar was added to the bottle, which was sealed and purged with nitrogen. The contents were heated at 160° C. while being purged with nitrogen overnight on an oil batch. The product from the reaction was further dried at 100° C. with a vacuum oven overnight.

Example 18

Synthesis of Triethylenetetramine Octanoic Acid Tetramide

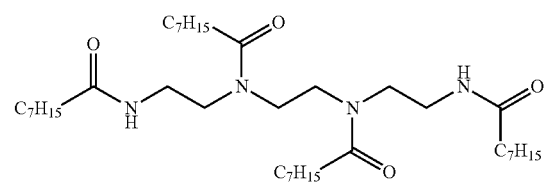

A sample of 7.31 g of triethylenetetramine was gradually added to 30.0 g of octanoic acid in a glass bottle. A spin bar was added to the bottle, which was sealed and purged with nitrogen. The contents were heated at 160° C. while being purged with nitrogen overnight on an oil batch. The product from the reaction was further dried at 100° C. with a vacuum oven overnight.

Example 19

Compounding Plasticizer with RILSAN Nylon-12

A sample of 10 wt-% of plasticizer from each of Examples 15-17 was compounded with RILSAN Nylon-12 as described in Example 2. The mechanical properties of the film of the compounded resin were tested according to ASTM D638 and are shown in Table 2. The melting point (mp) and crystallinity was determined by DSC.

TABLE 2

Thermal and Mechanical Properties of Plasticized Nylon-12

| Plasticizer | Tensile Strength (psi) | Tensile Modulus (psi) | Elongation (%) | mp (° C.) | Crystallinity (% by DSC) |
|---|---|---|---|---|---|
| Example 16 | 8637 | 83455 | 258 | 175.6 | 24.6 |
| Example 17 | 8871 | 81308 | 263 | 175.5 | 25.2 |
| Example 18 | 9079 | 95902 | 238 | 176.2 | 26.7 |
| Nylon-12 | 10931 | 167910 | 286 | 177.7 | 32.3 |

Example 20

Synthesis of N,N',N"-tridecanoyl diethylenetriamine

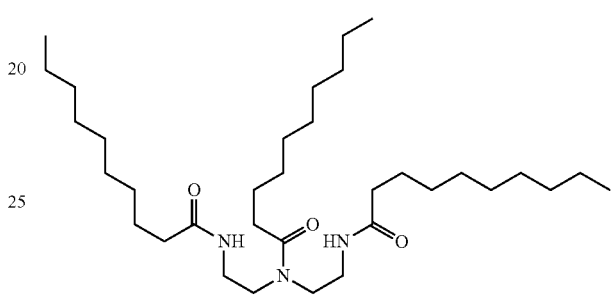

A sample of 5.76 g of diethylenetetramine was gradually added to 30.0 g of decanoic acid in a glass bottle. A spin bar was added to the bottle, which was sealed and purged with nitrogen. The contents were heated at 160° C. while being purged with nitrogen overnight on an oil batch. The product from the reaction was further dried at 100° C. with a vacuum oven overnight

Example 21

Synthesis of the Diethylenetriamine Triamide with Mixed Chain Length

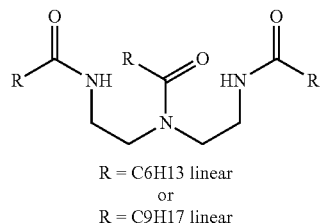

R = C6H13 linear
or
R = C9H17 linear

A sample of 7.0 g of diethylenetetramine was gradually added to 20.0 g of heptanoic acid and 10 g of decanoic acid in a glass bottle. A spin bar was added to the bottle, which was sealed and purged with nitrogen. The contents were heated at 160° C. while being purged with nitrogen overnight on an oil batch. The product from the reaction was further dried at 100° C. with a vacuum oven overnight

Example 22

Compounding Plasticizer with RILSAN Nylon-12

A sample of 10 wt-% of plasticizer from each of Examples 4-5 and 19-20 was compounded with RILSAN Nylon-12 as described in Example 2. The mechanical properties of the films of the compounded resin were tested according to ASTM D638 and are shown in Table 3. The melting point (mp) and crystallinity was determined by DSC.

TABLE 3

Thermal and Mechanical Properties of Plasticized Nylon-12

| Plasticizer | Tensile Strength (psi) | Tensile Modulus (psi) | Elongation (%) | mp (° C.) | Crystallinity (% by DSC) |
|---|---|---|---|---|---|
| Example 4 | 7422 | 66588 | 231 | 175.2 | 29.8 |
| Example 5 | 7411 | 74935 | 226 | 176.0 | 29.2 |
| Example 20 | 8034 | 83517 | 251 | 175.9 | 31.0 |
| Example 21 | 7674 | 67445 | 243 | 175.4 | 29.3 |
| Nylon-12 | 10931 | 167910 | 286 | 1777 | 32.3 |

Example 23

Synthesis of bis(3-aminopropyl)amine octanoic acid triamide

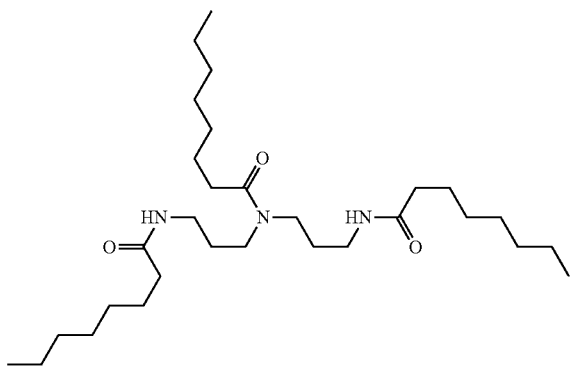 [SMILES: CCCCCCCC(=O)NCCCN(CCCNC(=O)CCCCCCC)C(=O)CCCCCCC]

A sample of 8.75 g of bis(3-aminopropyl)amine was gradually added to 30.0 g of octanoic acid and in a glass bottle. A spin bar was added to the bottle, which was sealed and purged with nitrogen. The contents were heated at 160° C. while being purged with nitrogen overnight on an oil batch. The product from the reaction was further dried at 100° C. with a vacuum oven overnight.

Example 24

Compounding Plasticizer with RILSAN Nylon-12

Figure 10:
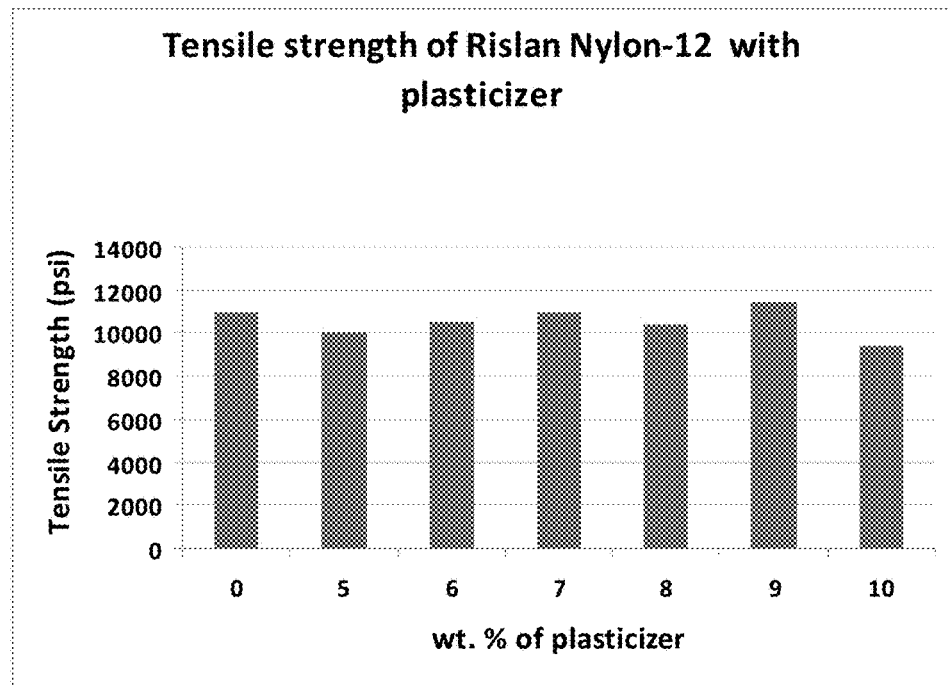
FIG. 10 is a graph of the tensile strength of an exemplary plasticized Nylon-12 (Example 24)
Figure 11:
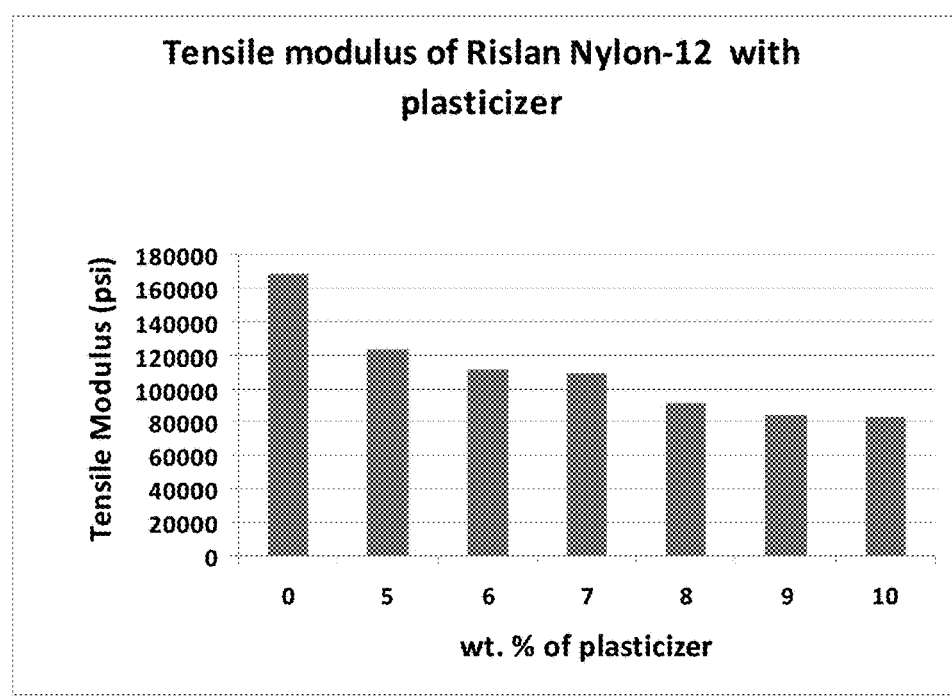
FIG. 11 is a graph of the tensile modulus of an exemplary plasticized Nylon-12 (Example 24).

A sample of 5-10 wt-% in RILSAN Nylon-12 was compounded with 5-10 wt-% plasticizer from Example 8 under similar conditions as in Example 9. Sheets (30-mils thick) were pressed at 200° C. from pellets. Tensile specimens were punched and tested on an INSTRON testing machine at a cross-head speed of 2 inches/minute according to ASTM D638 test Method. The results are summarized in FIG. 10 and FIG. 11. The tensile strength did not change with plasticizer content within experimental error, while the tensile modulus decreased with increasing plastic content.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. A medical device comprising a plasticized nylon which forms at least a portion of the medical device, wherein the plasticized nylon comprises a nylon mixed with an amide-containing plasticizer selected from a compound having the following structural formulas:

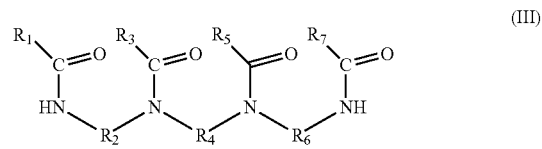

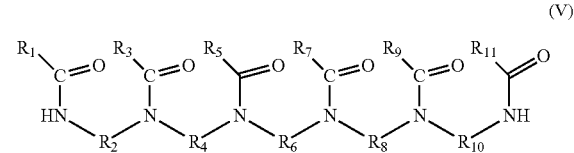

and combinations thereof;
wherein:
each $R_1$, $R_3$, $R_5$, $R_7$, $R_9$, and $R_{11}$ is independently selected from a C2-C18 linear, branched, or cyclic monovalent aliphatic group, a C5-C12 monovalent aromatic group, and combinations thereof; and
each $R_2$, $R_4$, $R_6$, $R_8$, and $R_{10}$ is independently selected from a C2-C18 linear, branched, or cyclic divalent aliphatic group, a C5-C12 divalent aromatic group, and combinations thereof.

2. The medical device of claim 1 wherein each $R_1$, $R_3$, $R_5$, $R_7$, $R_9$, and $R_{11}$ is independently selected from a C6-C12 linear, branched, or cyclic alkyl group.

3. The medical device of claim 2 wherein each $R_1$, $R_3$, $R_5$, $R_7$, $R_9$, and $R_{11}$ is independently selected from a C7-C8 linear, branched, or cyclic alkyl group.

4. The medical device of claim 1 wherein each $R_2$, $R_4$, $R_6$, $R_8$, and $R_{10}$ is independently selected from a C2-C4 linear, branched, or cyclic alkylene group.

5. The medical device of claim 1 wherein the plasticizer has the following structure:

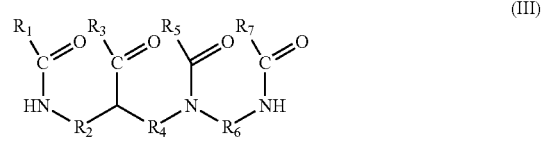

wherein:
each $R_1$, $R_3$, $R_5$, and $R_7$ is independently selected from a C2-C18 linear, branched, or cyclic alkyl group, a C5-C12 monovalent aromatic group, and combinations thereof; and
each $R_2$, $R_4$, and $R_6$ is independently selected from a C1-C5 linear alkylene group, a C5-C12 divalent aromatic group, and combinations thereof.

6. The medical device of claim 1 wherein the nylon is selected from the group of Nylon-6, Nylon-7, Nylon-8, Nylon-9, Nylon-10, Nylon-11, Nylon-12, Nylon-13, Nylon-14, Nylon-15, Nylon-16, Nylon-17, Nylon-18, Nylon-6,6, Nylon-6,8, Nylon-6,10, Nylon-6,12, Nylon-6,14, Nylon-8,8, Nylon-8,10, Nylon-8,12, Nylon-8,14, Nylon-10,10, Nylon-10,12, Nylon-10,14, Nylon-12,12, Nylon-12,14, Nylon-14,16, and combinations thereof.

7. The medical device of claim 1 wherein the amide-containing plasticizer is present in an amount of at least 0.1 wt-%, based on the total weight of the plasticized nylon.

8. The medical device of claim 7 wherein the amide-containing plasticizer is present in an amount of up to 50 wt-%, based on the total weight of the plasticized nylon.

9. The medical device of claim 1 wherein the amide-containing plasticizer is prepared from an amine and a fatty acid in a stoichiometric amount.

10. The medical device of claim 1 which is a dilatation balloon.

11. The medical device of claim 10 which is a catheter.

12. The medical device of claim 5 which is a balloon dilatation catheter, comprising:
a tubular elongated catheter shaft having proximal and distal portions; and
a dilatation balloon disposed on said shaft, wherein the shaft and/or balloon comprises the plasticized nylon.

13. The catheter of claim 12 further comprising a stent disposed on the balloon.

14. The medical device of claim 10 wherein the nylon is selected from the group of Nylon-6, Nylon-7, Nylon-8, Nylon-9, Nylon-10, Nylon-11, Nylon-12, Nylon-13, Nylon-14, Nylon-15, Nylon-16, Nylon-17, Nylon-18, Nylon-6,6, Nylon-6,8, Nylon-6,10, Nylon-6,12, Nylon-6,14, Nylon-8,8, Nylon-8,10, Nylon-8,12, Nylon-8,14, Nylon-10,10, Nylon-10,12, Nylon-10,14, Nylon-12,12, Nylon-12,14, Nylon-14,16, and combinations thereof.

15. The medical device of claim 10 wherein the amide-containing plasticizer is present in an amount of at least 0.1 wt-%, based on the total weight of the plasticized nylon.

16. The medical device of claim 15 wherein the amide-containing plasticizer is present in an amount of up to 50 wt-%, based on the total weight of the plasticized nylon.

17. The medical device of claim 10 wherein the amide-containing plasticizer is selected to decrease the flexural modulus and/or tensile modulus of the nylon and is used in an amount of 1 wt-% to 50 wt-%, based on the total weight of the plasticized nylon.

18. The medical device of claim 6 wherein the nylon is selected from the group of Nylon-10, Nylon-11, Nylon-12, Nylon-10,10, Nylon-10,12, and combinations thereof.

19. A medical device comprising a plasticized nylon which forms at least a portion of the medical device, wherein the medical device is a balloon, wherein the plasticized nylon comprises a nylon and 0.1 wt-% to 50 wt-% of an amide-containing plasticizer, based on the total weight of the plasticized nylon, wherein the plasticizer is mixed within the nylon and has the following structure:

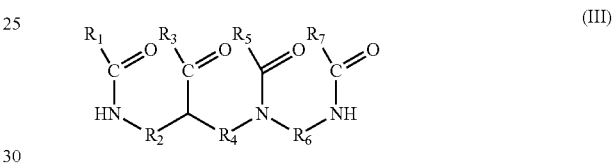

(III)

wherein:
each $R_1$, $R_3$, $R_5$, and $R_7$ is independently selected from a C7-C8 linear, branched, or cyclic alkyl group; and
each $R_2$, $R_4$, and $R_6$ is independently selected from a C1-C5 linear alkylene group, a C5-C12 divalent aromatic group, and combinations thereof.

20. The medical device of claim 1 wherein the amide-containing plasticizer is selected to decrease the flexural modulus and/or tensile modulus of the nylon and is used in an amount of 1 wt-% to 50 wt-%, based on the total weight of the plasticized nylon.

* * * * *